United States Patent
Ren et al.

(10) Patent No.: US 10,444,199 B2
(45) Date of Patent: Oct. 15, 2019

(54) EVANESCENT-WAVE QUARTZ-ENHANCED PHOTOACOUSTIC SENSOR WITH RESONATOR ELEMENTS

(71) Applicant: The Chinese University of Hong Kong, Hong Kong (CN)

(72) Inventors: Wei Ren, Hong Kong (CN); Zhili Li, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 36 days.

(21) Appl. No.: 15/483,638

(22) Filed: Apr. 10, 2017

(65) Prior Publication Data
US 2017/0292935 A1    Oct. 12, 2017

Related U.S. Application Data

(60) Provisional application No. 62/319,899, filed on Apr. 8, 2016.

(51) Int. Cl.
G01N 29/24    (2006.01)
G01N 29/02    (2006.01)

(52) U.S. Cl.
CPC ....... *G01N 29/2425* (2013.01); *G01N 29/022* (2013.01); *G01N 2291/021* (2013.01)

(58) Field of Classification Search
CPC .......... G01N 2291/021; G01N 29/022; G01N 29/2425
See application file for complete search history.

(56) References Cited

U.S. PATENT DOCUMENTS

| 7,245,380 | B2 | 7/2007 | Kosterev |
| 7,446,877 | B2 | 11/2008 | Li et al. |
| 7,605,922 | B2 | 10/2009 | Willing |
| 8,040,516 | B2 | 10/2011 | Van Kesteren et al. |
| 8,056,368 | B2 * | 11/2011 | Harper .............. C03B 37/15 65/381 |
| 2003/0109055 | A1 * | 6/2003 | Lehmann ............ G01J 3/42 436/164 |
| 2009/0174884 | A1 * | 7/2009 | Kosterev ......... G01N 21/1702 356/432 |

(Continued)

FOREIGN PATENT DOCUMENTS

CN    104568764 A  *  4/2015

OTHER PUBLICATIONS

Cao, Yingchun, Wei Jin, and Hoi Lut Ho. "Gas detection with evanescent-wave quartz-enhanced photoacoustic spectroscopy." Third Asia Pacific Optical Sensors Conference. vol. 8351. International Society for Optics and Photonics, 2012.*

(Continued)

*Primary Examiner* — Daniel S Larkin
(74) *Attorney, Agent, or Firm* — Saliwanchik, Lloyd & Eisenschenk

(57) ABSTRACT

A novel evanescent-wave quartz-enhanced optical microfiber photoacoustic gas sensor is provided for detecting trace amounts of gas. Both fiber-taper based evanescent field and photoacoustic spectroscopy can be used to exploit the merits of both technologies. The use of a fiber half-taper into the tuning fork and microresonator tubes can result in reduced system size, simplified optical alignment, and high sensitivity. The techniques described can be used in chemical, biological and environmental sensing applications.

16 Claims, 4 Drawing Sheets

(56) References Cited

U.S. PATENT DOCUMENTS

| | | | | |
|---|---|---|---|---|
| 2010/0116035 A1* | 5/2010 | Anderson | ............ | G01N 29/022 73/61.49 |
| 2011/0088453 A1 | 4/2011 | Nicoletti et al. | | |
| 2013/0299474 A1* | 11/2013 | Kashiwagi | .............. | H01S 3/067 219/121.81 |
| 2016/0266110 A1* | 9/2016 | Ozdemir | ............ | G01N 15/1434 |

OTHER PUBLICATIONS

A. Kosterev et al., Quartz-enhanced photoacoustic spectroscopy, Optics Letters, Nov. 1, 2002, pp. 1902-1904, vol. 27, No. 21, Optical Society of America.

Y. Cao et al., Evanescent-wave photoacoustic spectroscopy with optical micro/nano fibers, Optic Letters, Jan. 15, 2012, pp. 214-216, vol. 37, No. 2, Optical Society of America.

K. Liu et al., Off-beam quartz-enhanced photoacoustic spectroscopy, Optic Letters, May 15, 2009, pp. 1594-1596, vol. 34, No. 10, Optical Society of America.

Xuan et al., Long-period gratings in wavelength-scale microfibers, Optic Letter, Jan. 1, 2010, pp. 85-87, vol. 35, No. 1, Optical Society of America.

A. Kosterev et al., Applications of quartz tuning forks in spectroscopic gas sensing, Review of Scientific Instruments, 2005, pp. 1-9, vol. 76, 043105, http://dx.doi.org/10.1063/1.1884196, AIP Publishing.

G. Stewart et al., Prospects for fibre-optic evanescent-field gas sensors using absorption in the near-infrared, Sensors and Actuators B, 1997, pp. 42-47, 38-39, Elsevier Science S.A.

L. Dong et al., QEPAS spectrophones: design, optimization, and performance, Applied Physics B, 2010, pp. 627-635, 100, Springer-Verlag.

P. Patimisco et al., Quartz-Enhanced photoacoustic Spectroscopy: A Review, Sensors, 2014, pp. 6165-6206, 14, www.mdpi.com/journal/sensors, by the authors.

M. Tabib-Azar et al., Highly sensitive hydrogen sensors using palladium coated fiber optics with exposed cores and evanescent field interactions, Sensors and Actuators B, 1999, pp. 158-163, 56, Elsevier Science S.A.

W. Jin et al., Robust microfiber photonic microcells for sensor and device applications, Optics Express, 2014, pp. 28132-28141, vol. 22, No. 23, Optical Society of America.

Li, Z. et al., "Optical fiber tip-based quartz-enhanced photoacoustic sensor for trace gas detection", *Applied Physics B.*, May 2016, 122(147):1-6, Springer-Verlag Berlin Heidelberg 2016.

* cited by examiner

EVANESCENT-WAVE QUARTZ-ENHANCED PHOTOACOUSTIC SENSOR WITH RESONATOR ELEMENTS

CROSS-REFERENCE TO RELATED APPLICATION

This application claims the benefit of U.S. Provisional Application Ser. No. 62/319,899, filed Apr. 8, 2016, the disclosure of which is hereby incorporated by reference in its entirety, including all figures, tables and drawings.

FIELD OF THE INVENTION

The invention relates to a photoacoustic gas sensor based on the combination of evanescent-wave absorption using an optical microfiber with an acoustic oscillator and resonator elements.

BACKGROUND

Photoacoustic spectroscopy detection is applied for the analysis of various media including solids, liquids, biological tissues, and gases. Photoacoustic gas sensors operate by detecting acoustic vibrations induced by the modulated optical radiation in an analyzed gas sample. Quartz-enhanced photoacoustic spectroscopy (QEPAS) is one of the most sensitive photoacoustic detection techniques using an oscillator like a quartz tuning fork as the sharply resonant acoustic transducer. This method was first presented by A. Kosterev et al. (Opt. Lett. 27, 1902-1904 (2002) and U.S. Pat. No. 7,245,380 B2). QEPAS detection is less sensitive to environmental noise and has the advantages of small size, low cost, and ease of fabrication compared with traditional photoacoustic gas sensors. Numerous QEPAS-based gas sensors have been developed for various gas sensing applications with a normalized noise equivalent absorption (NNEA) coefficient in the range of $10^{-10}$-$10^{-7}$ cm$^{-1}$ WhiFiz as reviewed in Sensors 14, 6165 (2014) The previous QEPAS sensors using on-beam or off-beam detection schemes (A. Kosterev et al., Opt. Lett. 27, 1902 (2002); K. Liu et al., Opt. Lett. 34, 1594 (2009)) have mostly adopted the open-path optical configuration. Complicated optical alignment, a precise focusing system, and excitation sources with high spatial radiation quality were required to make the laser beam pass through a gap of 300-μm wide between the prongs of the quartz tuning fork and the micro-resonator tubes without touching any surfaces. An additional visualization system is sometimes required for the sensor setup.

Gas absorption by an evanescent field has been demonstrated with a palladium film deposited at a core-exposed fiber (M. Tabib-Azar el al., Sensor. Actuat. B-Chem. 56, 158 (1999)) or the D-shaped optical fiber (G. Stewart et al., Sensor. Actuat. B-Chem. 38; 42 (1997)). The sensitivity of evanescent-wave sensors is determined by the fraction of the optical power in the evanescent field. In the D-fiber evanescent-wave absorption sensor used for methane detection, due to the inherently low evanescent field, an extra sot-gel process was applied to coat the flat surface of the D-fiber to enhance the sensitivity. In the evanescent-wave hydrogen sensor, by depositing palladium over an exposed core region of a multimode fiber, the hydrogen can be detected based on evanescent field interaction with the palladium coating. However, microfibers made by the mechanical processing or chemical etching methods mentioned above suffer from the issue of fragility, Microfihers can also be obtained using the flame-brushing technique as described in Opt. Lett. 35, 85 (2010). The silica fiber taper fabricated using the flame-brushing method has the advantages of a high evanescent field and good mechanical properties.

The tapered microfibers provide an alternative method for photoacoustic detection with evanescent field interactions. A $C_2H_2$ photoacoustic sensor using tapered microfibers has been demonstrated by employing a full-taper optical fiber. However, only a bare quartz tuning fork was used in that sensor without micro-resonators. This caused a much lower sensitivity compared to the traditional open-path QEPAS sensors as presented by Y. Cao et al. in Opt Lett 37, 214-216 (2012).

BRIEF SUMMARY

The subject invention combines the fiber-taper based evanescent field with photoacoustic detection using oscillator and resonator elements and exploits the advantages of both techniques to achieve ultra-sensitive, compact, low-cost evanescent-wave gas sensors.

Embodiments of the subject invention provide microfiber photoacoustic detection devices for detecting the concentration of trace amounts of a target gas. A device can include a laser source tuned to the wavelength corresponding to the optical absorption of the target gas, a single mode fiber coupled with the laser for light delivery, a fiber-taper to generate evanescent waves for acoustic wave generation, an oscillator like quartz tuning fork to detect the acoustic waves, and/or micro-resonators positioned near the quartz tuning fork to enhance the acoustic signal.

The previous evanescent-wave fiber sensor can be employed for gas sensing, but requires a very long microfiber (meter to hundred meters) to achieve sufficient detection sensitivity. Traditional photoacoustic gas sensors using a quartz tuning fork as the acoustic transducer can achieve a compact and low-cost sensor configuration, but require complicated optical alignment and laser sources with high spatial radiation quality. The subject invention merges the fiber-taper based evanescent field and photo-acoustic spectroscopy and exploits the merits of both. The adoption of a fiber taper into the quartz tuning fork and micro-resonators significantly reduces system size, simplifies optical alignment, and achieves high sensitivity. This spectroscopic technique can be widely used in chemical, biological, and environmental sensing applications.

DETAILED DISCLOSURE OF THE INVENTION

Embodiments of the subject invention provide tnicrofiber photoacoustic detection devices for detecting the concentration of trace amounts of a target gas. A device can include a laser source tuned to the wavelength corresponding to the optical absorption of the target gas, a single mode fiber coupled with the laser for light delivery, a fiber-taper to generate evanescent waves for acoustic wave generation, an oscillator like quartz tuning fork to detect the acoustic waves, and/or micro-resonators positioned near the quartz tuning fork to enhance the acoustic signal.

Optical microfibers can be employed for robust light delivery and realize optical interconnection between optical devices on the microscale or nanoscale. The strong evanescent field generated by microfibers can also lead to high detection sensitivity for optical sensing applications. If an optical fiber without cladding is surrounded by gas that absorbs at the light wavelength, the evanescent wave penetrates into the region outside the fiber and transfers energy into the gas molecules. The use of an evanescent field for gas and liquid sensing has the advantages of low optical loss, easy alignment, and the potential of making integrated devices.

Figure 1:
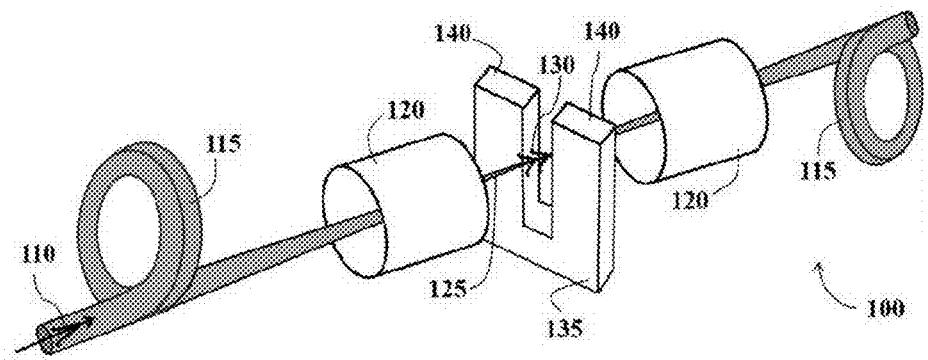
FIG. 1 shows a principle block diagram of a photoacoustic gas sensor comprising microfiber, turning fork, and resonator elements.

The principle of the photoacoustic gas sensor according to an embodiment of the subject invention, comprising a microfiber, a turning fork, and resonator elements, is illustrated generally at 100 in schematic form in FIG. 1. A fiber-taper 125 is inserted through two acoustic resonator tubes 120 and placed between the two prongs 140 of the quartz tuning fork 135 without touching any surfaces. The two resonator tubes 120 can be made of, for example, stainless steel and their lengths can be optimized for the first longitudinal mode resonance of the quartz tuning fork, for example, at the frequency of 32.7 kHz. The resonator tubes 120 act as an acoustic resonator to enhance the detection signal compared to the use of a bare tuning fork 135. In one embodiment, the resonator tubes enhance the detection signal by ~30 times. The incident laser radiation is guided by the single-mode fiber 115 to the taper section 125 to form an evanescent wave 130. The generated optical evanescent field 130 is confined closely around the fiber taper 125 to be absorbed by gas molecules.

The following steps are designed to facilitate the assembly of the microfiber with the quartz tuning fork and acoustic resonators. First, a visible laser diode (typical wavelength of 650 nm) can be employed as the light source 110 to connect with the input fiber 115, The visible light leaking out of the fiber taper 125 can be observed. In this way, the position of the fiber-taper 125 can be easily adjusted so that the evanescent field 130 between the two prongs 140 of the quartz tuning fork 135 has the maximum power density. Then, the visible light can be switched to an infrared laser with its emission wavelength coincident with the absorption line of the target gas. Compared with the traditional open-path quartz-enhanced photoacoustic system (U.S. Pat. No. 7,245, 380 B2,), the optical windows of the gas cell is eliminated in this technique. The evanescent wave 130 is confined closely around the fiber-taper leading to negligible optical noise, which enhances the detection sensitivity.

A large fraction of power existing in the evanescent field is required in this technique because the photoacoustic signal is proportional to the optical excitation power. The evanescent field 130 is related to the diameter of the fiber taper 125: the thinner the fiber diameter, the stronger the evanescent field. Thus, an ultrathin single mode fiber can be used to achieve high sensitivity.

If a fiber taper is placed between the two prongs of the quartz tuning fork 135 to generate evanescent-wave absorption, in the case of an optically thin gas sample, the detected acoustic signal S can be expressed as:

$$S = k\gamma\alpha x P_0 Q/F_0, \quad (Eq. 1)$$

where $\alpha$ ($cm^{-1}$/(molecule $cm^{-3}$) is the absorption coefficient of the target species; x (molecular/$cm^{-3}$) is the species concentration; $P_0$ (W) is the incident optical power; Q and $f_0$ (Hz) are the quality factor and the resonant frequency of the quartz tuning fork, respectively; $\gamma$ ($\gamma$<1) is the attenuation coefficient of the incident optical power associated with evanescent field; and k is a dimensionless coefficient describing the system parameters and acoustic transfer function. Therefore, a fiber taper with larger $\gamma$ is required to obtain a stronger photoacoustic signal.

Figure 2:
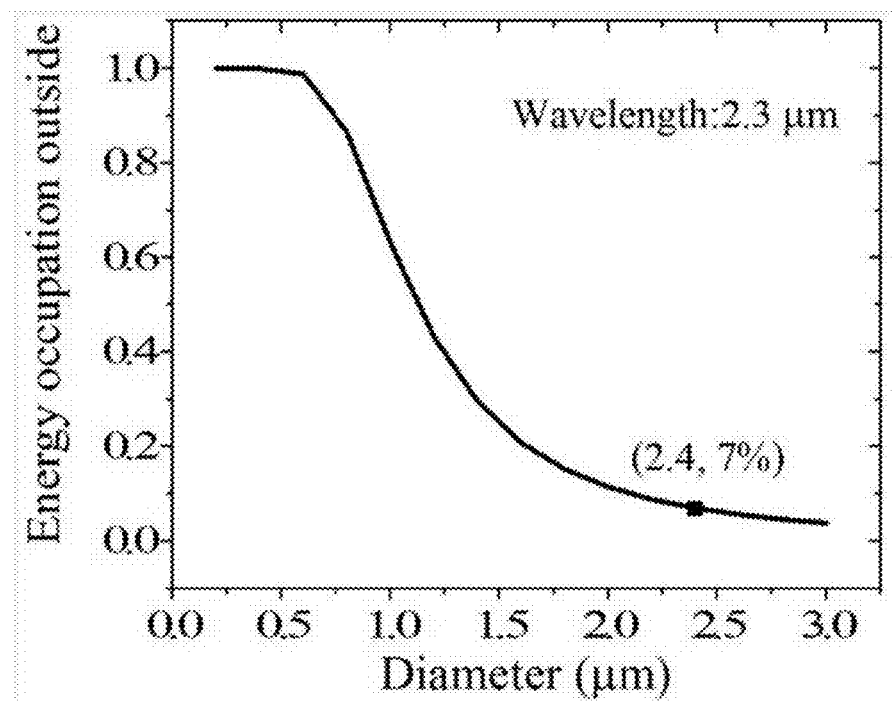
FIG. 2 shows the calculated ratio of the power in the evanescent wave to that of the total propagating wave as a function of fiber-taper diameter.

FIG. 2 presents at 200 the calculated percentage of optical power outside the fiber associated with the evanescent field 130 as a function of the fiber-taper diameter with an incident laser wavelength of 2.3 µm. According to Eq. 1, an ultrathin fiber taper 125 should be used to obtain a stronger evanescent field and thus to increase the photoacoustic signal.

Figure 3:
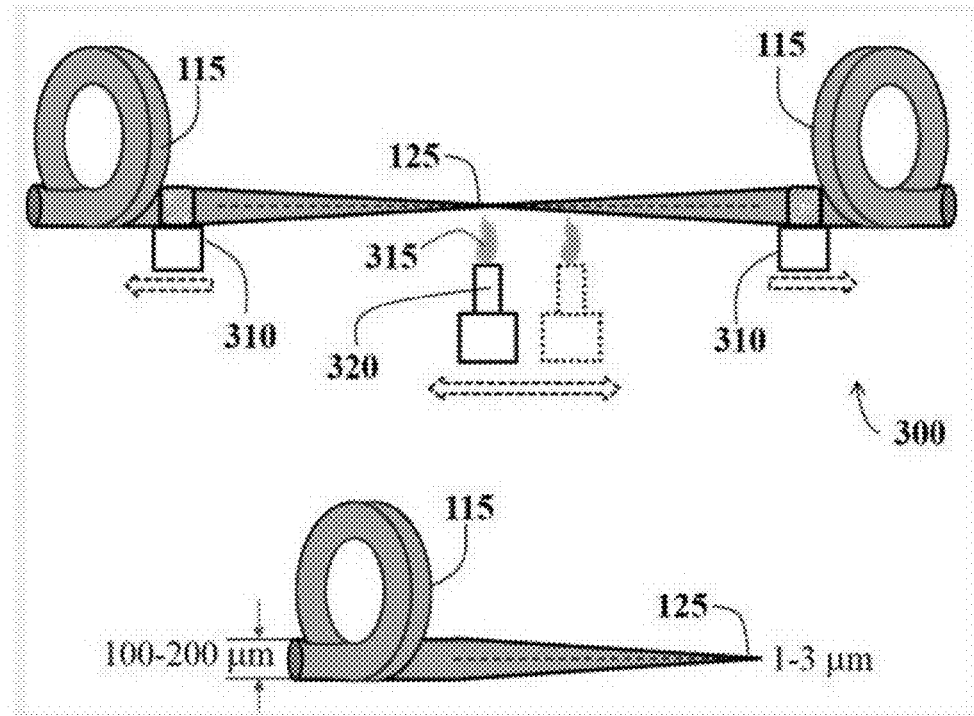
FIG. 3 shows a principle block diagram of a flame-brushing method to fabricate a fiber-taper.

FIG. 3 shows a principle block diagram 300 of using the flame-brushing method to fabricate a microfiber. The optical fiber 115 with low transmission loss at the laser emission wavelength is selected with the coating layer in the center section being stripped. The two ends of the fiber are fixed on two separate coaxial 1-D translation stages 310. A controlled hydrogen-flame 315 is placed under the stripped section for heating, while the translation stages 310 are moved in the opposite direction to stretch the fiber. The flame 315 is controlled to move along the fiber back and forth. By controlling the flame speed and fiber stretching rate, the fiber taper 125 with its diameter down to sub-wavelength scale (a few microns) can be fabricated. With the optimized parameters selected, a robust fiber taper 125 can be obtained for sensing applications.

Figure 4:
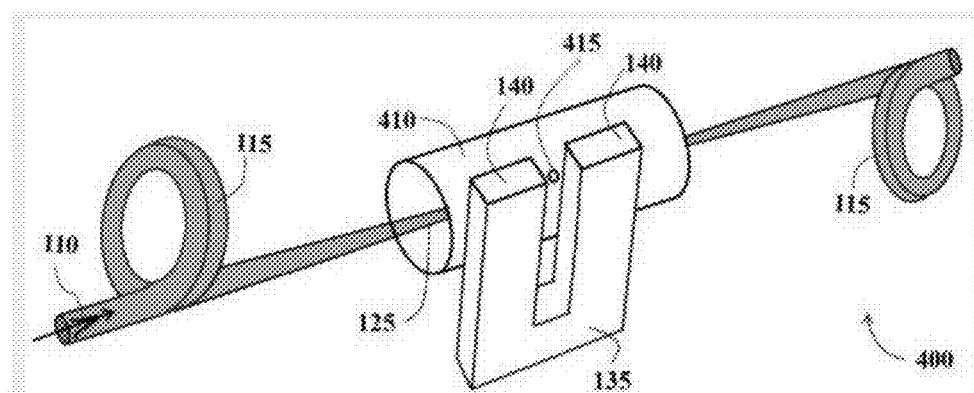
FIG. 4 shows a schematic view of a microfiber photoacoustic sensor with a small hole/slit opened in the center of a single resonator tube for acoustic detection.

In an embodiment, the quartz tuning fork can be integrated with the resonator tube using an alternative configuration. Different from the configuration 100 shown in FIG. 1, a single resonator tube can be utilized with a small hole or slit opened in the center of the tube. The quartz tuning fork can be placed nearby the hole/slit for the acoustic detection. The microfiber based evanescent field 130 is also suitable for this photoacoustic detection scheme. FIG. 4 depicts a schematic view 400 of such a sensor configuration with a microfiber. The fiber taper 125 is inserted through the single resonator tube 410 without touching any surfaces. Following the resonant acoustic pressure anti-node for the first longitudinal mode as described by K. Liu et al. (Opt Lett 34, 1594-1596 (2009)), a small hole or slit 415 is opened in the center of the resonator tube 410 for acoustic detection. The quartz tuning fork 135 is placed next to the resonator tube 410 to detect the acoustic wave leaked out of the small hole/slit 415.

Figure 5:
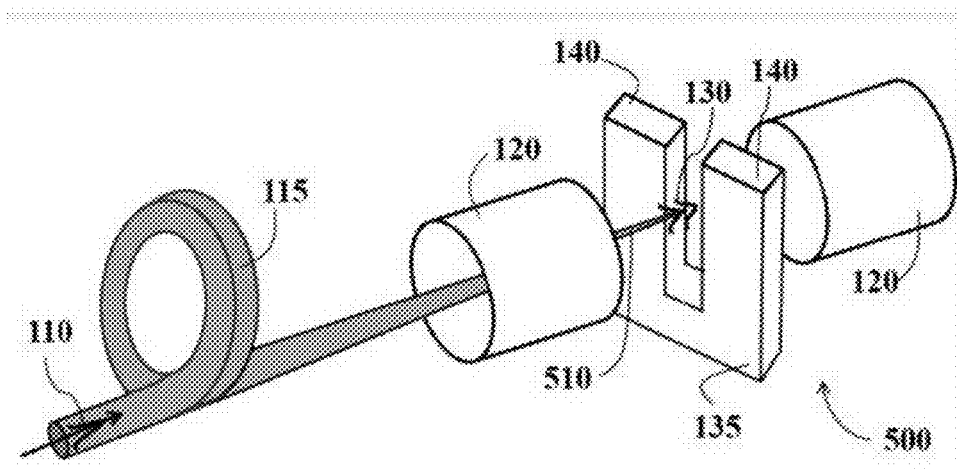
FIG. 5 shows a schematic view of a photoacoustic sensor using a fiber half-taper.

In an embodiment of the subject invention, a fiber half-taper with applications in a near-field scanning optical microscope can also be used in microfiber-based photoacoustic detection. FIG. 5 shows a schematic view 500 of a photoacoustic gas detector using a fiber half-taper, quartz tuning fork and micro-resonator tubes. The fiber half-taper 510 fabricated using the same flame-brushing method as discussed with respect to FIG. 3 can be inserted through the resonator tube 120 and placed between the two prongs of the quartz tuning fork 140. Compared with the system 100 described in with respect to FIG. 1, the fiber-taper 510 only passes through the first resonator tube 120.

In a particular embodiment, a silica-core single mode fiber 115 of 11-μm core, 125-μm cladding and a typical attenuation of 0.25 dB/m at the optical wavelength of 2.3 μm is selected. The optimized parameters of flame scanning length down to 1 mm and scanning speed of 0.2 mm/s are selected to obtain a fiber half-taper 510 in length of 14 mm and taper angle of 0.25°. The laser radiation 110 is guided through the single mode fiber 115 to the half-taper 510 that is integrated with the quartz tuning fork 135 and micro-resonator tubes 120 for the photoacoustic detection.

Figure 6:
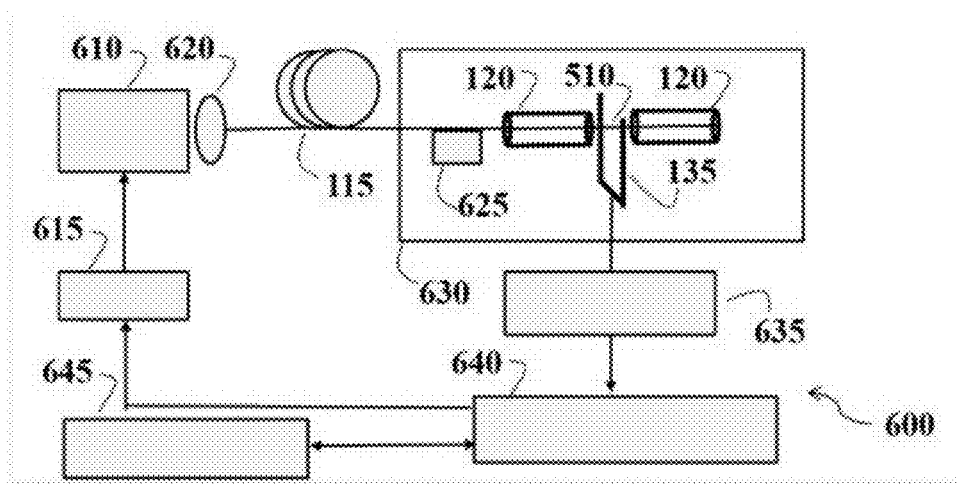
FIG. 6 shows a schematic diagram of the optical, mechanical and electronic layout of the photoacoustic detection system.

A photoacoustic sensor for CO detection is illustrated in FIG. 6, and can comprise a continuous-wave distributed feedback laser, a microfiber, a turning fork, a resonator, and a data acquisition and signal processing system. The distributed feedback laser 610 emitting at 2.3 μm can be used as the optical source to detect the CO absorption line centered at 4297.70 cm$^{-1}$. Wavelength modulation spectroscopy with the second harmonic (2f) detection can be implemented to enhance the detection sensitivity. A voltage ramp (e.g., 1 Hz) can be applied to the laser current driver 615 to scan the laser wavelength across the absorption line while a sinusoidal dither is applied at half of the resonant frequency (16.3 kHz) of the quartz tuning fork.

The free-space laser beam can be coupled into the single mode fiber 115 by employing an aspheric lens 620 fixed on a multi-axis translation stage. The single mode fiber 115 can be connected with the fiber half-taper 510 that is placed on a stage 625. In one embodiment, the laser wavelength is 2.3 μm and the fiber-taper diameter is 2.4 μm leading to about 7% of the incident optical power leaking out of the fiber core. In another embodiment, a fiber-coupled laser is employed and such an optical coupling system is not required. The CO molecules surrounding the fiber taper 510 absorb the modulated optical energy of the evanescent field 130 that leads to an acoustic wave, which is amplified by the resonator tubes 120. The generated acoustic wave excites the fundamental piezoelectric mode of the quartz tuning fork 135, thereby generating a weak current that is further amplified by a transimpedance amplifier 635. The pre-amplified signal can subsequently be demodulated at the resonant frequency of the tuning fork to obtain its component using a lock-in amplifier 640. All the data acquisition and signal processing operations can be controlled (e.g., via a LabVIEW program) by a computing device 645, such as a laptop computer.

Figure 7:
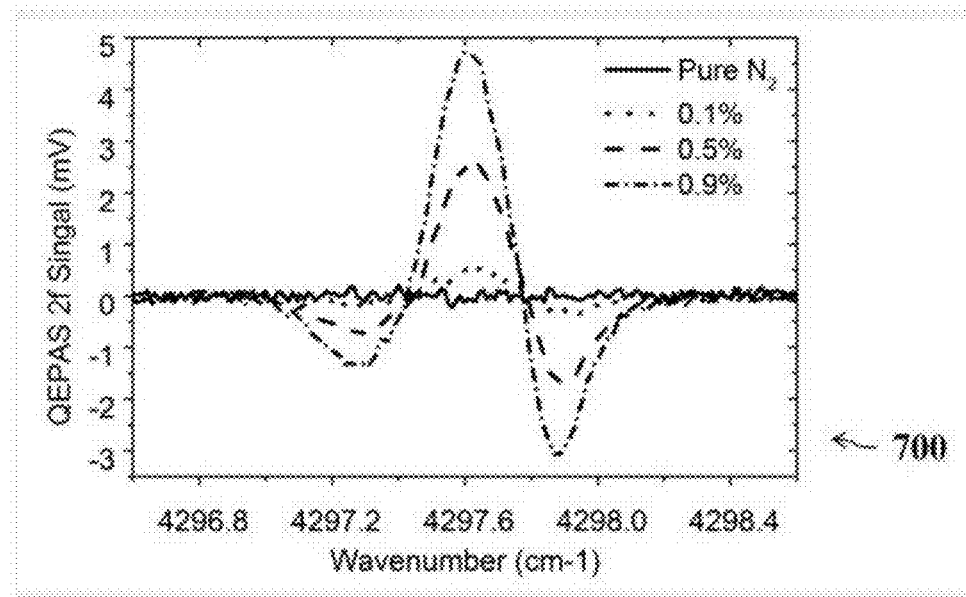
FIG. 7 illustrates representative signals of CO in $N_2$ at different concentrations.

Referring to FIG. 7 at 700, the evanescent-wave based quartz-enhanced photoacoustic gas detection device of an embodiment of the subject invention was used to acquire representative 2f signals using the lock-in amplifier at different CO concentrations (Pure $N_2$, 0.1%, 0.5% 0.9%, respectively). The noise level of the sensor was detected by introducing pure $N_2$ into the gas cell. Advantageously, the same noise level is observed by monitoring the 2f signals with the laser being turned off and on, respectively.

Figure 8:
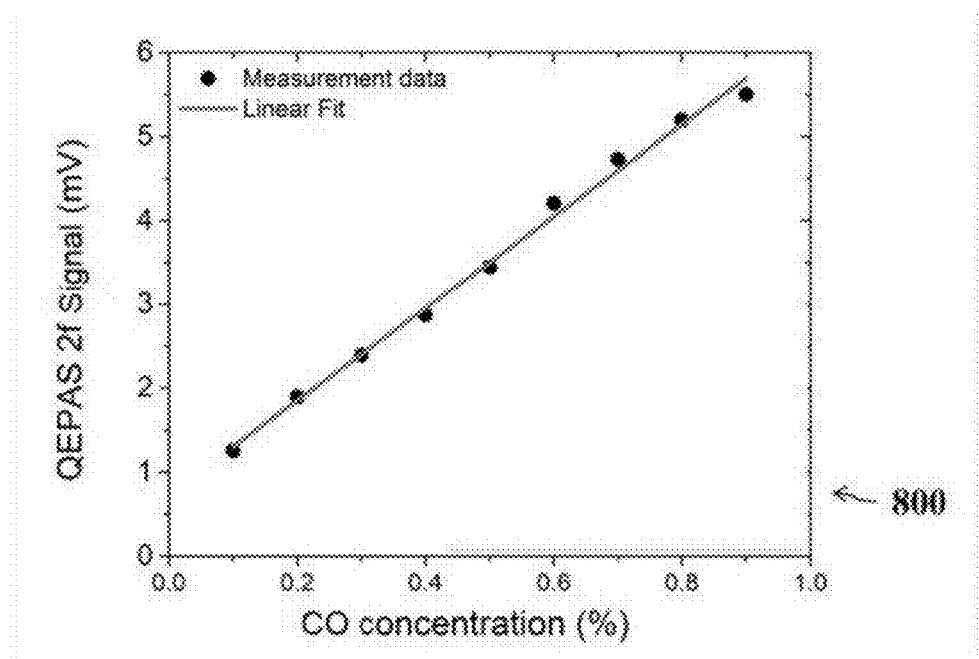
FIG. 8 illustrates examples of the measured sensor output signals as a function of the CO gas concentration.

Referring to FIG. 8 at 800, the representative 2f peak amplitude acquired using the evanescent-wave based quartz-enhanced photoacoustic gas detection device of the instant invention is depicted as a function of CO concentration (0.1-0.9%). A linear fit to the experimental data yields an R-square value of 0.998, indicating an excellent linear response of the sensor to the CO concentrations. A normalized noise equivalent absorption coefficient (NNEA) of $8.6 \times 10^{-8}$ cm$^{-1}$ W/N/Hz is achieved in the microfiber-based photoacoustic sensor of an embodiment of the subject invention, and this is competitive with the open-path quartz-enhanced photoacoustic detection systems. Thus, the detection sensitivity of the evanescent-wave based quartz-enhanced photoacoustic gas detection device of embodiments of the subject invention is competitive with traditional open-path QEPAS sensor systems and improved by >20 times with respect to a bare quartz tuning fork sensor without micro-resonators Advantageously, the evanescent-wave quartz-enhanced photoacoustic sensor of embodiments of the subject invention requires neither a focusing lens and visualization system for optical alignment, nor an optical window, In one embodiment, the evanescent-wave quartz-enhanced photoacoustic sensor is fixed inside a compact gas cell equipped with a gas inlet and outlet.

In a specific embodiment, water vapor is added into the gas mixture as a relaxation promoter to enhance the vibration-translation relaxation, thereby enhancing the photoacoustic signal. To this end, the testing gas mixture, before being introduced into the gas cell, is passed through a permeation tube that is immersed inside a water circulating bath. Advantageously, a typical relative humidity of 46% maintained in the gas flow constantly enhances the photoacoustic signal by a factor of approximately 3.

All patents, patent applications, provisional applications, and publications referred to or cited herein (including those in the "References" section) are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

A. Kosterev et al., Opt. Lett. 27, 1902-1904 (2002).
U.S. Pat. No. 7,245,380 B2.
K. Liu et al., Opt. Lett. 34, 1594 (2009).
M. Tabib-Azar et al, (Sensor. Actuat. B-Cheer. 56, 158 (1999)).
G. Stewart et al., Sensor. Actuat. B-Chem. 38, 42 (1997).
Opt. Lett. 35, 85 (2010).
Y. Cao et al., Opt Lett 37, 214-216 (2012).
U.S. Pat. No. 7,605,922 B2.
U.S. Pat. No. 8,040,516 B2.
U.S. Patent Application Publication No. 2011/0088453 A1.
U.S. Pat. No. 7,446,877 B2.
A. Kosterev, et al., Rev. Sci. Instrum. 76, 043105 (2005).
P. Patimisco et al., Sensors 14, 6165 (2014).
A. Dudus et al., IEEE J. Sel. Topics Quantum Electron, 22, 1 (2016).
W. Jin et al., Opt. Express 22, 28132 (2014).
L. Dong et al., Appl. Phys. B 100, 627 (2010).

We claim:

1. An evanescent-wave quartz enhanced microfiber photoacoustic detection device with oscillator and micro-resonator elements for detecting trace gas concentrations, the evanescent-wave quartz enhanced microfiber photoacoustic detection device comprising:

a light source tuned to a wavelength corresponding to the optical absorption of a gas to be detected;

an optical fiber;

a fiber-taper to generate an evanescent wave, a coating layer of the fiber-taper being stripped;

a quartz tuning fork having its free arms arranged at the level of the fiber-taper to absorb a mechanical force generated following the optical absorption by the gas, the mechanical force exciting a piezoelectric mode of the quartz tuning fork and generating an electrical current;

a micro-resonator disposed adjacent to the quartz tuning fork and configured to enhance the mechanical force;

a transimpedance amplifier amplifying a current generated by the quartz tuning fork to determine the concentration of the gas; and a lock-in amplifier directly connected to the transimpedance amplifier, wherein the fiber-taper, quartz tuning fork, and micro-resonator are assembled in a sealed gas cell for gas detection.

2. The device of claim 1, wherein the light source is an incident laser guided through the optical fiber into the fiber-taper.

3. The device of claim 2, wherein the fiber-taper is movable with respect to the quartz tuning fork.

4. The device of claim 1, wherein the fiber-taper is fabricated with a diameter of wavelength or subwavelength scale from a single mode fiber using a flame-brushing method.

5. The device of claim 1, wherein the fiber-taper is inserted into the micro-resonator and placed between two prongs of the quartz tuning fork without touching any surfaces.

6. The device of claim 5, wherein the micro-resonator is made of stainless steel and a length of the micro-resonator is set for a first longitudinal mode resonance of the acoustic wave.

7. The device of claim 1, wherein the fiber-taper is inserted into the micro-resonator, and the micro-resonator includes a small hole/slit opening.

8. The device of claim 7, wherein the quartz tuning fork is placed next to the hole/slit opening of the micro-resonator.

9. A method of photoacoustic detection, the method comprising:

providing the device of claim 1;

amplifying a current generated by the quartz tuning fork; and detecting the current generated by the quartz tuning fork.

10. The method of claim 9, wherein the light source is an incident laser guided through the optical fiber into the fiber-taper.

11. The method of claim 10, wherein the fiber-taper is movable with respect to the quartz tuning fork.

12. The method of claim 9, wherein the fiber-taper is fabricated with a diameter of wavelength or subwavelength scale from a single mode fiber using a flame-brushing method.

13. The method of claim 9, wherein the fiber-taper is inserted into the micro-resonator and placed between two prongs of the quartz tuning fork without touching any surfaces.

14. The method of claim 13, wherein the micro-resonator is made of stainless steel and a length of the micro-resonator is set for a first longitudinal mode resonance of the acoustic wave.

15. The method of claim 9, wherein the fiber-taper is inserted into the micro-resonator, and the micro-resonator includes a small hole/slit opening.

16. The method of claim 15, wherein the quartz tuning fork is placed next to the hole/slit opening of the micro-resonator.

* * * * *

UNITED STATES PATENT AND TRADEMARK OFFICE
CERTIFICATE OF CORRECTION

PATENT NO. : 10,444,199 B2
APPLICATION NO. : 15/483638
DATED : October 15, 2019
INVENTOR(S) : Wei Ren and Zhili Li Page 1 of 1

It is certified that error appears in the above-identified patent and that said Letters Patent is hereby corrected as shown below:

In the Specification

Column 1,
Line 38, "WhiFiz" should read --$W/\sqrt{Hz}$--.
Line 58, "extra sot-gel" should read --extra sol-gel--.
Line 66, "fragility, Microfihers" should read --fragility. Microfibers--.

Column 3,
Line 6, "tnicrofiber" should read --microfiber--.
Line 38, "of 32.7 kHz" should read --of ~32.7 kHz--.

Column 5,
Lines 44-45, "obtain its component" should read --obtain its 2f component--.
Line 66, "WIN/Hz" should read --$W/\sqrt{Hz}$--.

Column 6,
Line 49, "B-Cheer." should read --B-Chem.--.

Signed and Sealed this
Second Day of June, 2020

Andrei Iancu
*Director of the United States Patent and Trademark Office*